United States Patent [19]

Arend et al.

[11] 4,327,040
[45] Apr. 27, 1982

[54] PREPARATION OF PHOSPHORIC ACID PROPARGYL ESTERS

[75] Inventors: Günter Arend, Dormagen; Peter Feyen, Mettmann, both of Fed. Rep. of Germany

[73] Assignee: Bayer Aktiengesellschaft, Leverkusen, Fed. Rep. of Germany

[21] Appl. No.: 158,032

[22] Filed: Jun. 9, 1980

[30] Foreign Application Priority Data

Jul. 2, 1979 [DE] Fed. Rep. of Germany ....... 2926652

[51] Int. Cl.³ .................... C07F 9/113; C07F 9/173
[52] U.S. Cl. ..................................... 260/973; 260/956
[58] Field of Search .......................... 260/973

[56] References Cited

U.S. PATENT DOCUMENTS

| | | | |
|---|---|---|---|
| 2,471,464 | 5/1949 | Toy et al. | 260/973 |
| 2,865,801 | 12/1958 | Baker et al. | 260/973 |
| 3,005,001 | 10/1961 | Senkbeil | 260/973 |
| 3,087,957 | 4/1963 | Senkbeil | 260/973 |
| 3,189,636 | 6/1965 | Boisselle | 260/973 |
| 3,336,422 | 8/1967 | Peterson | 260/973 |
| 3,972,887 | 8/1976 | Freedman | 260/973 |
| 4,007,197 | 2/1977 | Freedman et al. | 260/973 |

Primary Examiner—Anton H. Sutto
Attorney, Agent, or Firm—Sprung, Felfe, Horn, Lynch & Kramer

[57] ABSTRACT

A process for the preparation of a phosphoric acid propargyl ester of the formula

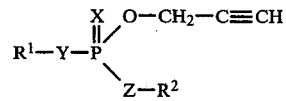

wherein
$R^1$ and $R^2$ each independently is an aryl radical or a $C_{1-4}$-alkyl, $C_{1-4}$-alkenyl or $C_{1-4}$-alkynyl radical, and
X, Y and Z each independently is oxygen or sulphur, comprising reacting a phosphoric acid monoester chloride or diester chloride with at least the equivalent amount of propargyl alcohol in a two-phase system in the presence of an inorganic base as an acid-trapping agent, and a catalyst comprising about 0.001 to 100 mol %, relative to the phosphoric acid ester chloride, of a tertiary amine or quaternary ammonium or phosphonium salt with at least 9 C atoms. Advantageously the catalyst is present in about 0.01 to 10 mol % relative to the phosphoric acid ester chloride and is a tertiary amine or quaternary ammonium salt, X, Y and Z are oxygen, $R^1$ is propargyl and $R^2$ is $C_{1-4}$-alkyl, the reaction is effected in the presence of methylene chloride, chloroform or toluene as solvent, the base is used in at least the equivalent amount and is selected from the group consisting of alkali metal hydroxides, alkaline earth metal hydroxides, alkali metal carbonates and alkaline earth metal carbonates.

13 Claims, No Drawings

PREPARATION OF PHOSPHORIC ACID PROPARGYL ESTERS

The present invention relates to an unobvious process for the preparation of certain phosphoric acid propargyl esters.

Phosphoric acid esters, containing propargyl radicals, of the general formula

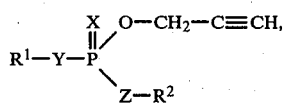

wherein

R$^1$ and R$^2$ independently of one another represent an aryl radical or a C$_{1-4}$-alkyl, C$_{1-4}$-alkenyl or C$_{1-4}$-alkynyl radical and X, Y and Z independently of one another denote oxygen or sulphur, have been disclosed, in addition to other compounds, as highly active insecticidal synergistic agents in European Patent Application 78 100 117.7.

A number of processes for the preparation of phosphoric acid esters are described in the literature, and a survey can be found in "Houben-Weyl, Methoden der Organischen Chemie (Methods of Organic Chemistry)," Volume 12/2, page 299 et seq. (1964). However, for the preparation of phosphoric acid propargyl esters, these processes can be used only to a limited extent and in general give poor yields.

Propargyl alcohol is only slightly reactive and, compared with saturated aliphatic alcohols or allyl alcohol, reacts only with great difficulty, especially with phosphoric acid diester chlorides.

Thus, for example, phosphorus oxychloride can be converted into tributyl phosphate to the extent of 85% with excess butanol at 50° C. without an acid-trapping agent. In contrast, the analogous reaction with phosphoric acid diethyl ester chloride and propargyl alcohol gives no amounts of propargyl ester which are capable of being isolated (see Comparison Example 6 below). The corresponding reaction with phosphorus oxychloride is also sluggish (see Comparison Example 7 below).

The reaction path from phosphorus oxychloride to phosphoric acid diethyl propargyl ester via phosphoric acid propargyl ester dichloride also gives an unsatisfactory overall yield of only 25% (see Comparison Example 7 below), and phosphoric acid dipropargyl ester chloride cannot be prepared at all without an acid-trapping agent being present; the reaction mixture decomposes on distillation.

If the reaction is carried out in the presence of at least equimolar amounts of acid-trapping agents, for example triethylamine, phosphoric acid ethyl dipropargyl ester is obtained in a maximum yield of 51% from phosphoric acid ethyl ester dichloride and propargyl alcohol (see Comparison Examples 1–5). Nitrogen-containing by-products are evidently formed in this process, since in spite of very careful washing with dilute sulphuric acid, a highly volatile, strongly basic decomposition product always condenses in the cold trap at −70° C. during the vacuum distillation. Accordingly, the distillation bottom product becomes strongly acid, and rapidly becomes resinous.

The reaction of saturated aliphatic alcohols, employed in excess, with phosphorus oxychloride or phosphoric acid alkyl ester dichlorides at temperatures below 30° C. in the presence of an at least equimolar amount of sodium hydroxide solution is described in Japanese patent application No. 7 7042-779. Trimethyl phosphate, for example, is obtained in 85% yield by this process. On attempting to react phosphoric acid ethyl ester dichloride with propargyl alcohol in an analogous manner, a maximum yield of 70% is obtained after a reaction time of up to 20 hours. If the organic phase is separated off by extraction with methylene chloride or chloroform and is washed with sodium carbonate solution and water, a pH value of 1–2 is constantly established when it is left to stand. The phosphorus chloride has evidently not been reacted quantitatively, and slowly splits off acid. If toluene is used for the extraction instead of methylene chloride or chloroform, the presence of chloride (after alcoholysis) can be detected with silver nitrate. If the reaction time is increased still further, the yield falls again owing to hydrolysis; in this context, see Comparison Examples 8 and 9.

The reaction of dialkyl phosphites with propargyl alcohol in the presence of excess carbon tetrachloride and of a tertiary amine, analogous to the method of G. H. Steinberg, J. Org. Chem. 15, 637 (1950), proceeds quite well. This reaction enables exclusively phosphoric acid monopropargyl esters to be prepared, but can be realized industrially only with difficulty. Recovering the amine which has reacted to give the hydrochloride and separating off and recovering the excess amine, the excess carbon tetrachloride and the chloroform formed demand an expensive unit. In addition, the reaction usually starts up after a delay and then proceeds at a high rate and in a highly exothermic manner, so that the heat of reaction can easily be removed in the laboratory but can be removed only with difficulty on an industrial scale.

It has now been found that the yield and purity in the preparation of phosphoric acid alkyl propargyl esters and phosphoric acid aryl propargyl esters can be further increased if the synthesis is carried out as a two-phase reaction in the presence of catalytic amounts of tertiary amines or quaternary ammonium or phosphonium salts with at least 9 C atoms, and an inorganic base in at least equimolar quantity is used as an acid-trapping agent.

The invention thus provides a process for the preparation of a phosphoric acid propargyl ester of the general formula

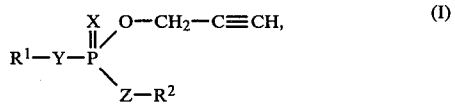

in which

R$^1$ and R$^2$ independently of one another represent aryl or a C$_{1-4}$-alkyl, C$_{1-4}$-alkenyl or C$_{1-4}$-alkynyl radical and X, Y and Z independently of one another denote oxygen or sulphur, characterized in that a phosphoric acid monoester chloride or diester chloride is reacted with at least the equivalent amount of propargyl alcohol in a two-phase system in the presence of an inorganic base an an acid-trapping agent, using about 0.001 to 100 mol %, preferably about 0.01 to 10 mol %, relative to phosphoric acid ester chloride, of a tertiary amine or quaternary ammonium or phosphonium salt with a total of at least 9 C atoms as the catalyst.

The process is preferably directed to the preparation of a compound (I) in which X, Y and Z each represent oxygen and/or in which $R^1$ represents the propargyl radical and $R^2$ represents $C_{1-4}$-alkyl.

The propargyl alcohol can be employed in this reaction in an excess of any desired amount. However, it is sufficient and thus preferable to limit the excess of propargyl alcohol to 0 to about 10 mol %, relative to phosphoric acid ester chloride.

In similar, but uncatalyzed, reactions, the aliphatic alcohol is usually employed in a large excess in order to keep the hydrolysis, which proceeds as a side reaction, of the phosphoric acid ester chloride and of the phosphoric acid triester formed as low as possible. Thus, for example, a 233% excess of methanol is employed in the Japanese Pat. No. 7 7042-779 quoted above. In contrast, if approximately equimolar amounts of alcohol are used, water must be largely excluded during the esterification; in this context, see Houben Weyl, Methoden der Organischen Chemie (Methods of Organic Chemistry), Volume 12/2, instructions pages 315-321. Against this background, it was not to be expected that phosphoric acid esters can be prepared in good purity and in yields of up to 96% by the reaction of phosphoric acid ester halides with propargyl alcohol, which is not very reactive, by the process according to the invention, even if the propargyl alcohol is employed in only a slight excess of 0 to 10 mol %.

If a tertiary amine is used as the catalyst, this is preferably added to the batch to the extent of about 1 to 10 mol %, and about 0.01 to 1 mol % of quaternary ammonium or phosphonium salt suffices; the mol % in each case is relative to phosphoric acid ester chloride. The tertiary amines can be removed quantitatively from the organic phase by acid extraction. To isolate the phosphoric acid propargyl esters, which in some cases are heat-labile, it is thus only necessary to wash the organic phase of the reaction mixture adequately, and to subject it to incipient distillation or a stripping operation to remove low-boiling constituents and, if appropriate, solvents. The phosphoric acid ester can be isolated as the residue in outstanding yield and purity.

However, the catalytically more active quaternary ammonium or phosphonium salts predominantly remain in the organic phase in a non-extractable form, and the organic phase must thus be purified, preferably by distillation.

The reaction temperature can be from about $-10°$ to $+80°$ C., preferably between $0°$ and $+40°$ C. A high reaction temperature favors hydrolysis of the phosphoric acid ester chloride and of the phosphoric acid ester and thus decreases the yield.

In a preferred embodiment of the process according to the invention, the propargyl alcohol is initially introduced into the reaction vessel together with the catalyst and, if appropriate, some of the solvent used. A solution of the phosphoric acid ester chloride in two parts by volume of the organic solvent and an aqueous solution of the inorganic base are allowed to run in simultaneously through separate inlets in the course of 1 to 5 hours, while cooling and while stirring intensively. The mixture is subsequently stirred for a further 0.5 to 25 hours, the salt which has separated out is filtered off, if appropriate, and the phases are separated. The organic phase is washed with water and, if appropriate, dried with an inert agent. The solvent is distilled off and the crude product which remains can be further purified by vacuum distillation in a thin film evaporator or by fractional distillation over a column.

In principle, it is also possible to carry out the reaction without adding an auxiliary solvent. Because both the phosphoric acid ester chlorides and the phosphoric acid propargyl esters prepared therefrom have a poor solubility in the propargyl alcohol/aqueous phase, the reaction proceeds as a two-phase boundary reaction and is accelerated by the catalysts used according to the invention. However, the yields which can be achieved are in general higher in the presence of inert organic diluents which are sparingly soluble in water. The following solvents, for example, can advantageously be used; halogenated hydrocarbons, such as methylene chloride, chloroform, carbon tetrachloride, dichloroethane, trichloroethylene, tetrachloroethylene, chlorobenzene and dichlorobenzene; hydrocarbons, such as benzene, toluene and xylene and blends thereof with aliphatic hydrocarbons; ethers, such as diethyl ether, dipropyl ether and dibutyl ether; substituted hydrocarbons, such as nitromethane, nitroethane, nitrobenzene and benzonitrile; ketones, such as methyl propyl ketone, methyl butyl ketone and methyl isobutyl ketone; and esters, such as ethyl acetate, propyl acetate, butyl acetate, ethyl propionate, propyl propionate and butyl propionate.

The inorganic bases used are, preferably, water-soluble alkali metal hydroxides and carbonates and alkaline earth metal hydroxides and carbonates, such as sodium hydroxide, potassium hydroxide, barium hydroxide, sodium bicarbonate, sodium carbonate and potassium carbonate. Alkaline earth metal bases which are sparingly soluble in water, such as magnesium carbonate, magnesium oxide, calcium oxide, calcium carbonate, barium oxide and barium carbonate, can also be used, but they are advantageously initially introduced into the reaction vessel together with the propargyl alcohol, water and catalyst and a suspension is formed.

The amount of water to be initially introduced is not very critical, and the initial water can even be dispensed with completely. A variant in which water is initially introduced in an amount such that a saturated salt solution is obtained as the aqueous phase at the end of the reaction has proved advantageous.

A selection of suitable catalysts for the process according to the invention is listed below: benzyldimethylamine, dibenzylmethylamine, benzyldiethylamine, benzyl-di-(2-cyanoethyl)-amine, tributylamine, tris-2-ethylhexylamine, stearyldimethylamine, tetrabutylammonium chloride, tricaprylmethylammonium chloride, tris-2-ethylhexyl-methylammonium chloride, trioctylmethylammonium chloride, trimethylphenylammonium chloride, trimethylbenzylammonium chloride, triethylbenzylammonium chloride, trimethylbenzylammonium hydroxide, benzyldodecyldimethylammonium chloride, stearyltrimethylammonium chloride, lauryltrimethylammonium chloride, myristyltrimethylammonium chloride, tetrabutylphosphonium chloride and triphenylmethylphosphonium bromide.

The Comparison Examples illustrate the results which are achieved in the preparation of phosphoric acid ethyl propargyl esters by known processes. The subsequent examples illustrate the process according to the invention.

Comparison Examples of the preparation of phosphoric acid propargyl esters using pyridine or triethylamine; general instructions 1 mol of the particular phosphoric acid ester chloride was added dropwise to a mixture of 500 ml of methylene chloride or toluene and, per equivalent of chlorine to be reacted, 1.1 mols of propargyl alcohol and 1.1 mols of the organic base (in each case corresponding to a 10% excess) at 10° to 20° C., while cooling. The mixture was subsequently stirred at room temperature for 2 hours and at about 40° C. for 2 hours, the amine hydrochloride was filtered off and the solution was washed first with 10% strength $H_2SO_4$ several times and then with water.

The product was isolated by vacuum distillation over a short column. Highly volatile, basic, nitrogen-containing decomposition products thereby escaped and were condensed in a cold trap at −70° C. The distillation bottom product accordingly gave a strongly acid reaction and rapidly became resinous.

Comparison Examples 1–5 of Table I were carried out according to these instructions.

Comparison Example 7

Phosphoric acid diethyl propargyl ester via phosphoric acid propargyl ester dichloride 1 mol of propargyl alcohol was added dropwise to 1.2 mols of phosphorus oxychloride at 35° C. The reaction was slightly exothermic and hydrogen chloride was evolved. The mixture was subsequently stirred at 50° C. for 1 hour and at 60° C. for 1 hour and was distilled. The product decomposed very easily.

Yield: 45% of phosphoric acid propargyl ester dichloride, undistilled.

Boiling point: 89°–91° C./21 mbars
$n_D^{20}$: 1.4683

1 mol of this undistilled dichloride was added dropwise to 4 mols of ethanol (100% excess) at 20°–30° C., while stirring and passing nitrogen through. The mixture was allowed to react at 25° C. for 2 hours and at 50° C. for 1 hour, the excess ethanol was distilled off in vacuo and the residue was washed with dilute sodium carbonate solution and water until neutral. On distillation, 4.3% of phosphoric acid ethyl propargyl ester chloride, 55.9% of phosphoric acid diethyl propargyl

TABLE I

| Comparison Example No. | Starting material | Base | Ester prepared | Boiling point | $n_D^{20}$ of the propargyl ester | Yield % |
|---|---|---|---|---|---|---|
| 1 | $POCl_3$ | Pyridine | $PO(OCH_2-C{\equiv}CH)_3$ | 105–108° C./0.1 mbar | 1.4682 | 9.7 |
| 2 | $(CH_3O)_2\overset{O}{\overset{\|}{P}}-Cl$ | Pyridine | $(CH_3O)_2\overset{O}{\overset{\|}{P}}OCH_2-C{\equiv}CH$ | 72° C./0.2 mbar | 1.4282 | 24.5 |
| 3 | $H_5C_2-O-PCl_2$ | $(H_5C_2)_3N$ | $H_5C_2-O-\overset{O}{\overset{\|}{P}}-(O-CH_2C{\equiv}CH)_2$ | 100° C./0.1 mbar | 1.4488 | 49.5 |
| 4 | $(CH_3-\underset{CH_3}{\underset{\|}{CH}}-O)_2-\overset{O}{\overset{\|}{P}}Cl$ | Pyridine | $(H_3C-\underset{CH_3}{\underset{\|}{CH}}-O)_2\overset{O}{\overset{\|}{P}}-CH_2-C{\equiv}CH$ | 100° C./3 mbar | 1.4270 | 51.0 |
| 5 | $i\text{-}H_9C_4O-\overset{O}{\overset{\|}{P}}Cl_2$ | $(H_5C_2)_3N$ | $n\text{-}H_9C_4-O-\overset{O}{\overset{\|}{P}}(O-CH_2-C{\equiv}CH)_2$ | 122° C./0.2 mbar | 1.4490 | 39.4 |

Comparison Examples of the preparation of phosphoric acid propargyl esters without using acid-trapping agents

Comparison Example 6

Phosphoric acid diethyl propargyl ester via phosphoric acid diethyl ester chloride 1 mol of phosphoric acid diethyl ester chloride was added dropwise to 1.2 mols of propargyl alcohol at 20°–30° C., while stirring and passing nitrogen through. The mixture was allowed to react at 20°–30° C. for 2 hours and at 50° C. for 1 hour and was then taken up in 500 ml of methylene chloride and the methylene chloride mixture was washed twice with dilute sodium carbonate solution and once with water. On distillation, 0.76 mol of phosphoric acid diethyl ester chloride (boiling point: 76°–53° C./0.6–0.7 mbar) was recovered and no phosphoric acid diethyl propargyl ester was isolated. If the reaction was carried out at 80° to 100° C. for 6 hours, about 15% of impure diethyl propargyl phosphate was obtained, boiling point: 70°–82° C./0.2 mbar.

ester and 4.0% of a higher-boiling component were obtained.

The yield of phosphoric acid diethyl propargyl ester over the two stages was thus 25.2%.

Comparison Examples of the preparation of phosphoric acid propargyl esters using sodium hydroxide solution as the base (analogously to the method of Japanese patent application No. 7 7042-779).

Comparison Example 8

Preparation of phosphoric acid diethyl propargyl ester with a large excess of propargyl alcohol in the presence of sodium hydroxide solution.

1 mol of phosphoric acid diethyl ester chloride and 1.07 mols of 50% strength sodium hydroxide solution were added dropwise to 3.33 mols of propargyl alcohol (233% excess) at 15°–20° C. The mixture was stirred for 15 minutes, water was added to dissolve the salt and the mixture was extracted with 800 ml of chloroform. On distillation, 70% of phosphoric acid diethyl propargyl ester was obtained.

Comparison Example 9

Repetition of Comparison Example 8, but with only a 3% excess of propargyl alcohol Yield: 61% of phosphoric acid diethyl propargyl ester.

Under the conditions of Comparison Examples 8 and, in particular, 9, the phosphoric acid chloride evidently reacted only incompletely. The solution of the crude product in chloroform constantly gave a strongly acid reaction after standing for several hours. If toluene was used for the extraction instead of chloroform, chloride could be detected in the organic phase with alcoholic silver nitrate solution, and this indicated the presence of unreacted phosphoric acid ester chloride.

Longer reaction times decreased the yield, and hydrolysis then evidently occurred.

Analogous reaction of phosphoric acid ethyl ester dichloride with 2.06 equivalents of propargyl alcohol proceeded with an even lower yield of 55%.

EXAMPLE 1 (according to the invention)

Phosphoric acid diethyl propargyl ester 1 mol of phosphoric acid diethyl ester chloride was initially introduced into a reaction vessel together with 4 g (1 mol %) of tricaprylmethylammonium chloride and 500 ml of chloroform. 1.1 mols of propargyl alcohol (10% excess) and 1.03 mols of NaOH, dissolved in 110 ml of water, were simultaneously added dropwise at 10° C. in the course of 30 minutes.

The mixture was stirred for a further 3 hours at 10° C. and the phases were separated. The organic phase was washed with dilute sodium carbonate solution and with 200 ml of water. The chloroform was distilled off under normal pressure. The yield, determined by gas chromatography (phosphoric acid triethyl ester as the internal standard) was 96.2%. After fractional distillation, 88.9% of phosphoric acid diethyl propargyl ester were obtained.

EXAMPLES 2 to 13: (according to the invention)

Phosphoric acid ethyl dipropargyl ester

General instructions 2.06 mols of propargyl alcohol, the amount indicated below of the particular catalyst and 250 ml of the particular solvent used were initially introduced into the reaction vessel. A solution of 1.0 mol of phosphoric acid ethyl ester dichloride in 2 parts by volume of the solvent and 2.2 mols of sodium hydroxide solution, as an approximately 20% strength solution in water, were allowed to run in simultaneously at 10° to 15° C. in the course of 3 hours. After 1 hour, the mixture was subsequently stirred at 10° to 15° C. The reaction mixture had to be alkaline, and if this was not the case, up to a further 0.2 mol of the dilute sodium hydroxide solution could be added.

After the phases had been separated, the organic phase was extracted with 200 ml of water. Low-boiling components, such as the solvent and the excess of propargyl alcohol, were stripped off in vacuo and the residue was dried with anhydrous potassium carbonate and filtered. According to analysis by gas chromatography, the crude product had a content of over 96%, and it could be further purified by thin film distillation.

The examples listed in Table II were carried out in this manner.

The yields listed in Table II below relate to 100% pure product and were determined by gas chromatography, against triethyl phosphate as the internal standard. On distillation, a product loss of 3 to 5% was to be reckoned with.

TABLE II

| Example No. | Catalyst (amount) | Solvent | Yield % |
|---|---|---|---|
| 2 | 0.3 mol % of tricaprylmethyl-ammonium chloride | $CH_2Cl_2$ | 87.5 |
| 3 | 0.06 mol % of tricaprylmethyl-ammonium chloride | $CH_2Cl_2$ | 92.5 |
| 4 | 0.06 mol % of tricaprylmethyl-ammonium chloride | — | 76.6 |
| 5 | 0.06 mol % of tricaprylmethyl-ammonium chloride | Toluene | 80.0 |
| 6 | 1.2 mol % of tricaprylmethyl-ammonium chloride | $CHCl_3$ | 84.5 |
| 7 | 0.06 mol % of benzyldodecyl-dimethylammonium chloride | $CH_2Cl_2$ | 84.5 |
| 8 | 0.06 mol % of tetrabutylammonium chloride | $CH_2Cl_2$ | 85.4 |
| 9 | 0.06 mol % of tetrabutylammonium chloride | Toluene | 75.3 |
| 10 | 0.06 mol % of benzyltriethyl-ammonium chloride | $CH_2Cl_2$ | 77.6 |
| 11 | 0.06 mol % of benzyltriethyl-ammonium chloride | Toluene | 83.4 |
| 12 | 5.0 mol % of benzyldimethylamine | $CH_2Cl_2$ | 85.9 |
| 13 | 5.0 mol % of benzyldimethylamine | Toluene | 78.8 |
| 14 | 5.0 mol % of triethylamine | Toluene | 67.2 |

Example 14, although the same general instructions were followed, was not according to the invention; in this example it was found that when a tertiary amine with less than 9 C atoms was used, no significant improvement compared with the uncatalyzed reaction described in Comparison Example 9 resulted.

EXAMPLE 15

Phosphoric acid propyl dipropargyl ester

Phosphoric acid propargyl ester dichloride was reacted with propargyl alcohol analogously to Example 3. Yield: 87.0%.

Boiling point: 105°–107° C./0.2 mm Hg.
$n_D^{20}$: 1.4512.

EXAMPLE 16

Thionophosphoric acid ethyl dipropargyl ester

Thionophosphoric acid ethyl ester dichloride was reacted with propargyl alcohol in toluene in the presence of 0.06 mol % of tricaprylmethylammonium chloride at 50° C. analogously to Example 5. The reaction had ended after 15 to 20 hours. The crude product was dried thoroughly over $CaCl_2$.

According to gas chromatography, thionophosphoric acid ethyl dipropargyl ester was obtained in 70.0% yield.

$n_D^{20}$: 1.4888.

Boiling point: 105° C./0.05 mm Hg. Purity, according to gas chromatography: 95.0%.

It will be appreciated that the instant specification and examples are set forth by way of illustration and not limitation, and that various modifications and changes may be made without departing from the spirit and scope of the present invention.

I claim:

1. A process for the preparation of a phosphoric acid propargyl ester of the formula

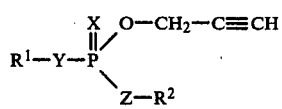

wherein
- $R^1$ and $R^2$ each independently is an aryl radical or a $C_{1-4}$-alkyl, $C_{1-4}$-alkenyl or $C_{1-4}$-alkynyl radical, and
- X, Y and Z each independently is oxygen or sulphur, comprising reacting a phosphoric acid monoester chloride or diester chloride with at least the equivalent amount of propargyl alcohol in a two-phase water-organic solvent system in the presence of an aqueous solution of an inorganic base as an acid-trapping agent, and a catalyst comprising about 0.001 to 100 mol %, relative to the phosphoric acid ester chloride, of a tertiary amine or quaternary ammonium or phosphonium salt with at least 9 C atoms.

2. A process according to claim 1, wherein the catalyst is present in about 0.01 to 10 mol % relative to the phosphoric acid ester chloride.

3. A process according to claim 2, wherein the catalyst is a tertiary amine.

4. A process according to claim 2, wherein the catalyst is a quaternary ammonium salt with at least 9 C atoms in the cationic part of the molecule and it is present in about 0.01 to 1 mol % relative to the phosphoric acid ester chloride.

5. A process according to claim 1, wherein X, Y and Z are oxygen.

6. A process according to claim 1, wherein $R^1$ is propargyl and $R^2$ is $C_{1-4}$-alkyl.

7. A process according to claim 1, wherein the reaction is effected in the presence of an inert substantially water-immiscible organic solvent selected from the group consisting of hydrocarbons, halogenated hydrocarbons, nitro-substituted hydrocarbons, ethers, ketones and esters.

8. A process according to claim 7, wherein the solvent comprises methylene chloride, chloroform or toluene.

9. A process according to claim 1, wherein the base is selected from the group consisting of alkali metal hydroxides, alkaline earth metal hydroxides, alkali metal carbonates and alkaline earth metal carbonates.

10. A process according to claim 1, wherein the base is used in at least the equivalent amount.

11. A process according to claim 1, wherein the reaction is effected at about $-10°$ C. to $+80°$ C.

12. A process according to claim 11, wherein the reaction is effected at about 0° to 40° C.

13. A process according to claim 9, wherein the catalyst is present in about 0.01 to 10 mol % relative to the phosphoric acid ester chloride and is a tertiary amine or quaternary ammonium salt, X, Y and Z are oxygen, $R^1$ is propargyl and $R^2$ is $C_{1-4}$-alkyl, the reaction is effected in the presence of methylene chloride, chloroform or toluene as solvent, the base is used in at least the equivalent amount and the reaction is effected at about 0° to 40° C.

* * * * *